(12) United States Patent
Orr et al.

(10) Patent No.: US 9,837,839 B2
(45) Date of Patent: Dec. 5, 2017

(54) PORTABLE DEVICE AND METHOD OF SUPPLYING POWER TO A PORTABLE DEVICE

(71) Applicant: Orrex Medical Technologies, LLC, Grapevine, TX (US)

(72) Inventors: Nicol Rae Orr, Kerrville, TX (US); David John Reed, Sheffield (GB)

(73) Assignee: ORREX MEDICAL TECHNOLOGIES, LLC, Grapevine, TX (US)

( * ) Notice: Subject to any disclaimer, the term of this patent is extended or adjusted under 35 U.S.C. 154(b) by 117 days.

(21) Appl. No.: 14/987,428

(22) Filed: Jan. 4, 2016

(65) Prior Publication Data

US 2016/0211688 A1    Jul. 21, 2016

(51) Int. Cl.
| | |
|---|---|
| *H02J 7/00* | (2006.01) |
| *A61B 17/16* | (2006.01) |
| *A61B 50/30* | (2016.01) |
| *A61B 50/33* | (2016.01) |
| *A61B 50/39* | (2016.01) |
| *A61B 17/00* | (2006.01) |
| *A61B 50/00* | (2016.01) |
| *A61B 90/00* | (2016.01) |

(52) U.S. Cl.
CPC ........ *H02J 7/0044* (2013.01); *A61B 17/1628* (2013.01); *A61B 50/30* (2016.02); *A61B 50/33* (2016.02); *A61B 50/39* (2016.02); *A61B 2017/0046* (2013.01); *A61B 2017/00398* (2013.01); *A61B 2017/00429* (2013.01); *A61B 2017/00734* (2013.01); *A61B 2050/0065* (2016.02); *A61B 2090/0813* (2016.02)

(58) Field of Classification Search
CPC ......... H02J 7/0044; H02J 7/007; H02J 7/0042
USPC .......................................................... 320/103
See application file for complete search history.

(56) References Cited

U.S. PATENT DOCUMENTS

| | | | |
|---|---|---|---|
| 6,181,105 B1 * | 1/2001 | Cutolo ................. | H02J 7/0042 320/115 |
| 2010/0114247 A1 * | 5/2010 | Snitting ................ | A61N 1/375 607/60 |
| 2012/0110810 A1 | 5/2012 | Houser et al. | |
| 2012/0112690 A1 * | 5/2012 | Stulen .............. | A61B 17/00234 320/108 |

OTHER PUBLICATIONS

PCT International Search Report for related PCT/US2016/012173, dated Mar. 18, 2016, 3 pages.
PCT Written Opinion of the International Search Authority for related PCT/US2016/012173, dated Mar. 18, 2016, 8 pages.

* cited by examiner

*Primary Examiner* — Nathaniel Pelton
(74) *Attorney, Agent, or Firm* — Polsinelli PC (57) ABSTRACT

A portable device and method of supplying power to the portable device may provide a sterile environment that may protect the health and safety of patients on whom the device is employed. The portable device may be charged inside of the sterile environment. The portable device may be charged using at least one chargeable battery that may be arranged internal and/or external to a portion of the portable device, or internal and/or external to the portable device. A power supply may be connected to the at least one chargeable battery and power the portable device for use. The portable device may be charged up to 100% and/or or fully charged prior to opening the sterile environment.

16 Claims, 6 Drawing Sheets

PORTABLE DEVICE AND METHOD OF SUPPLYING POWER TO A PORTABLE DEVICE

CROSS REFERENCE TO RELATED APPLICATIONS

This application claims the benefit under 35 U.S.C. §§119 (a) and (b) of Chinese Application No. CN2015233776U filed on Jan. 19, 2015, entitled "Portable Medical Sterile Charging Power Supply," Chinese Application No. CN2015233080U filed on Jan. 19, 2015, entitled "Medical Electric Saw Drill with Automatic Locking and Automatic Correcting Functions," Chinese Application No. CN20152337630U filed on Jan. 19, 2015, entitled "Medical Disposable Electric Saw-Drill," and Chinese Application No. CN2015233765U filed on Jan. 19, 2015, entitled "Medical Electrical Saw Drill with Anti-Shake Function." The content of each application is incorporated herein by reference in its entirety.

FIELD OF THE DISCLOSURE

The present disclosure generally relates to a power tool and a method of supplying power to a power tool, and more particularly to a portable device powered by a chargeable battery and a method of supplying power to the portable device powered by a chargeable battery.

BACKGROUND

Medical equipment and instruments are required to maintain an aseptic condition in order to protect the safety and health of patients. With the advancement of science and technology, using electrical medical equipment has become more common. However, one problem associated with using electrical medical equipment includes difficulty with safely transporting equipment over long-distances, thereby compromising the safety and health of patients that require electrical medical equipment. Additionally, prior to being shipped, medical equipment and instruments are typically only charged between 10% and 50% of their full capacity. As such, in order to ensure medical operations are safely performed, medical equipment and instruments must be charged and require a sterile power supply. In the event of an unexpected or tragic incident, e.g., an earthquake, typhoon, blizzard, or widespread power outage, charging medical equipment may not be possible. Further, geographic locations that do not have access to an adequate power supply and/or sterile environment cannot fully charge medical equipment and instruments.

While mobile power supplies are available, existing power supply devices and methods of supplying power are not able to charge medical equipment and instruments located in a sealed and sterile environment. Rather, these power supplies and methods thereof are surrounded by dust and bacteria, and are susceptible to contact by harmful fluids. Accordingly, the sterility and safety of using these power supplies to charge electrical medical equipment and instruments is degraded and the service life is significantly reduced. Additionally, the patient's health can be compromised.

SUMMARY

Embodiments of the present disclosure may provide a method for supplying power to a portable device that may be powered by at least one chargeable battery. The method may provide sealing the portable device in a sterile environment using a first microbial barrier, and the first microbial barrier may maintain the sterile environment. The method may provide charging the portable device in the sterile environment. A power supply may be arranged to supply power to the at least one chargeable battery contained in the portable device. The method may provide sealing the portable device in the sterile environment using a second microbial barrier. The second microbial barrier may provide protection in addition to the first microbial barrier to maintain the sterile environment. The method may provide arranging the at least one chargeable battery inside of a portion of the portable device, arranging the at least one chargeable battery external to the portion of the portable device, and/or arranging the at least one chargeable battery external to the portable device. The method may provide charging the portion of the portable device to a full capacity prior to opening the sterile environment.

Embodiments of the present disclosure may provide a portable device that may be powered by at least one chargeable battery. The portable device may provide at least one microbial barrier that may be arranged to seal the portable device, and the at least one microbial barrier may maintain a sterile environment for the portable device. The portable device may provide a portion of the portable device that may include a charging port, a first tray that may be configured to receive and secure the portion of the portable device, a second tray that may be configured to receive and secure the first tray, a package that may be configured to receive the second tray, and at least one chargeable battery. The at least one chargeable battery may be configured to power the portable device. At least one cable may connect the at least one chargeable battery to the charging port, and a power supply may be arranged to supply power to the at least one chargeable battery. The at least one chargeable battery may be arranged inside of the portion of the portable device, may be arranged external to the portion of the portable device, and/or may be arranged external to the portable device. The portable device may be charged to a full capacity prior to opening the sterile environment.

A system for supplying power to a portable device may be provided in a sterile environment. The system may provide securing a portion of the portable device in a first tray, and the portion of the portable device may include a charging port for receiving power. The system may provide covering the first tray with a first microbial barrier and connecting the portion of the portable device to the first tray using a first connecting cable. The system may provide securing the first tray in a second tray and covering the second tray with a second microbial barrier. Further, the system may provide connecting the first tray and the second tray using a second connecting cable and connecting the second tray to a package using a third connecting cable. The system may provide securing the second tray in the package and supplying power to the portable device using at least one chargeable battery. The at least one chargeable battery may be arranged inside of the portion of the portable device, may be arranged external to the portion of the portable device, and/or may be arranged external to the portable device. The portable device may be charged to a full capacity prior to opening the sterile environment.

Other technical features may be readily apparent to one skilled in the art from the following figures, descriptions and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

Figure 1:
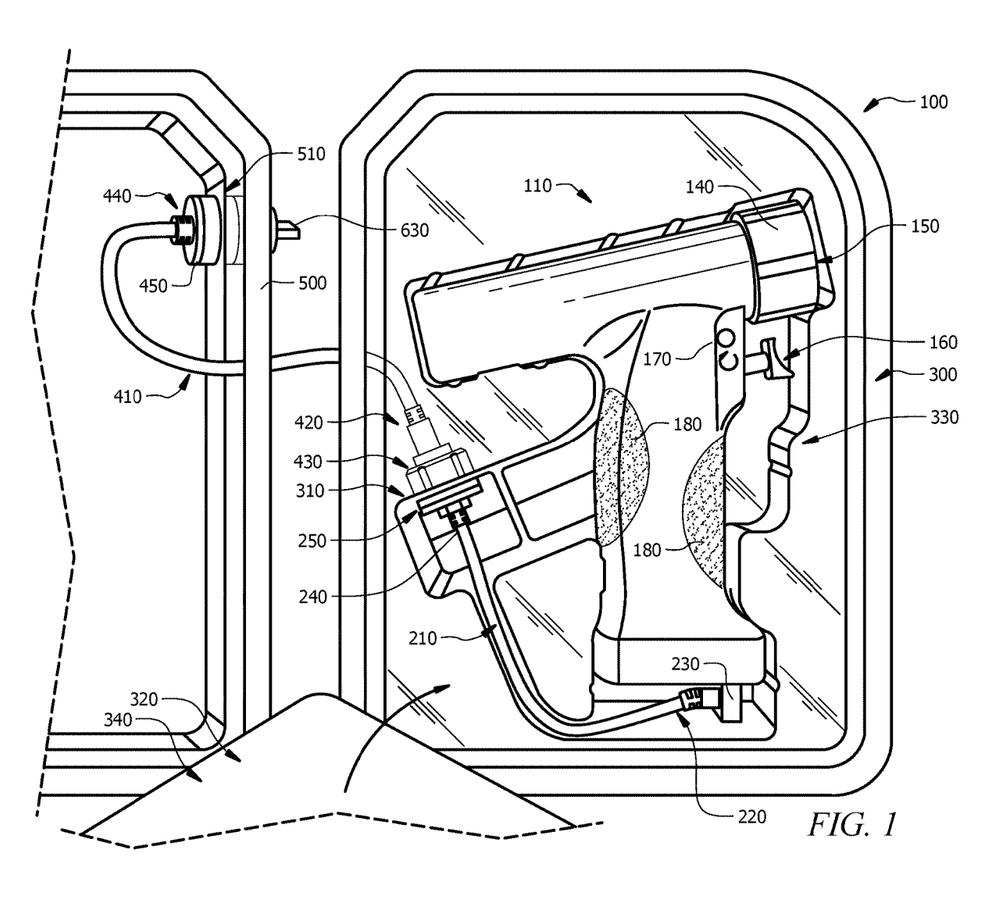
FIG. 1 depicts a portable device according to an embodiment of the present disclosure.

As shown in FIG. 1 according to an embodiment of the present disclosure, portable device that may be powered by at least one chargeable battery (hereinafter, "portable device") 100 may include portion 110 of portable device 100 that may be charged to a full capacity in a sterile environment and may be sealed by at least first microbial barrier 340. It should be appreciated that portable device 100 may be powered by a plurality of energy sources including, but not limited to, batteries and/or capacitors. Portion 110 may be secured within compartment 330 of first tray 300. Compartment 330 may be molded to the shape of portion 110 and the shape of first connecting cable 210, thereby securing portion 110 and first connecting cable 210 within first tray 300. It should be appreciated that portion 110 of portable device 100 may be a handpiece, a handle, or a gripping mechanism according to embodiments of the present disclosure. First tray 300 may be covered and sealed using first breathable lid or cover 320 and may be made from a material that may include first microbial barrier 340. First breathable lid or cover 320 may include first microbial barrier 340 to maintain a sterile environment for portable device 100. It should be appreciated that first microbial barrier 340 may provide sterile asepsis to eliminate micro-organisms from portable device 100. It should be appreciated that first tray 300 may be a blister pack that may be made of plastic or other similar material without departing from the present disclosure. It should be appreciated that first tray 300, second tray 500, and package 700 (FIG. 3 and FIG. 5) may prevent portable device 100 from sustaining damage during shipment. First connector 230 may include a male connector and may be provided at first end 220 of first connecting cable 210. It should be appreciated that a male connector may be a universal serial bus (USB), a male cord end, and/or male wire end without departing from the present disclosure. Second connector 250 of first connecting cable 210 may be provided at second end 240 opposite first end 220, and second end 240 may be secured within first wall 310 of first tray 300. Second connector 250 may include a female port that may be provided to receive third connector 430 of second connecting cable 410. It should be appreciated that a female port may include, but is not limited to, a USB port, a female cord end, and/or female wire end without departing from the present disclosure.

Figure 3:
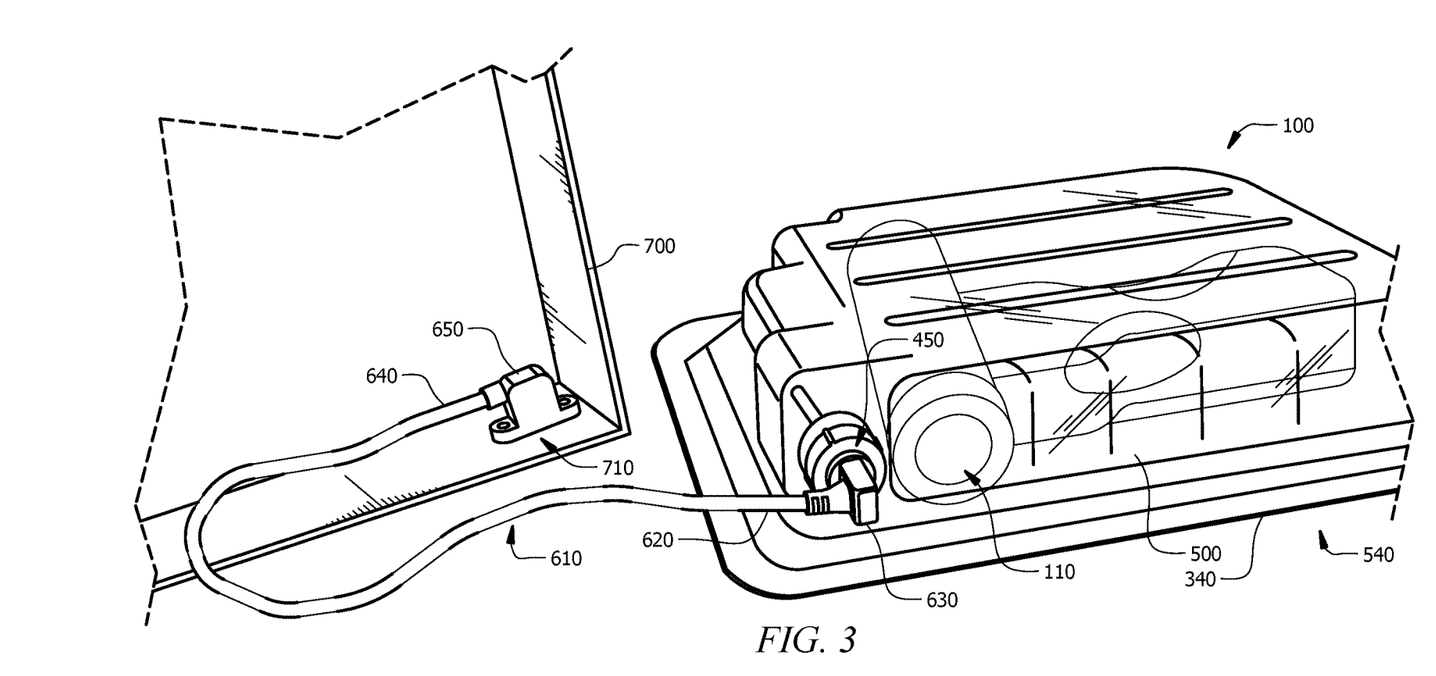
FIG. 3 depicts a perspective view of a portable device including microbial barriers and a package according to an embodiment of the present disclosure.

As shown in FIG. 1 according to an embodiment of the present disclosure, second connecting cable 410 may provide third connector 430, and third connector 430 may be provided at third end 420 of second connecting cable 410. Third connector 430 may include a male connector. Fourth connector 450 of second connecting cable 410 may include a female port that may be provided to receive fifth connector 630 of third connecting cable 610 (FIG. 3). It should be appreciated that first connecting cable 210 may be removed from within first wall 310 by disconnecting third connector 430 from second connector 250. Fourth connector 450 may be provided at fourth end 440 of second connecting cable 410 opposite third end 420. It should further be appreciated that second connecting cable 410 may be removed from within second wall 510 of second tray 500 by disconnecting fifth connector 630 from fourth connector 450. It should be appreciated that each connecting cable may be removed from a connection with a wall, package, or another connecting cable by unscrewing or disengaging each male-female connection. Second tray 500 may be covered and sealed using second breathable lid or cover 520 (FIG. 3) that may be made from a material that may include second microbial barrier 540 in some embodiments of the present disclosure. Second breathable lid or cover 520 may include second microbial barrier 540 to maintain a sterile environment for portable device 100. It should be appreciated that second microbial barrier 540 may provide sterile asepsis to eliminate micro-organisms from the portable device. It should be appreciated that cover 320 and cover 520 may provide a double layer of protective microbial barriers 340, 540 that may help to protect the sterility of portable device 100. It should be appreciated that a plurality of microbial barriers may be provided to create a sterile environment without departing from the present disclosure. It should further be appreciated that cover 320 and cover 520 may form a primary packaging for portable device 100 without departing from the present disclosure.

As shown in FIG. 1 according to an embodiment of the present disclosure, second wall 510 of second tray 500 may house a connection between fourth connector 450 and fifth connector 630. Fourth connector 450 may receive fifth connector 630. Fifth connector 630 may include a male connector. Sixth connector 650 may include a female port that may be accessible from an exterior of package 700 (FIG. 3) using sixth connector 650. It should be appreciated that a male connector may include, but is not limited to, a male USB connector, a male cord end, and/or male wire end, and a female port may include, but is not limited to, a female USB port, a female cord end, and/or female wire end without departing from the present disclosure. Portable device 100 may be charged while inside of package 700, first tray 300, and second tray 500 by connecting power supply 800 (FIG. 4) to sixth connector 650 in embodiments of the present disclosure.

It should be appreciated that package 700, first tray 300 and second tray 500 may create a sterile barrier system (SBS). It should be appreciated that the SBS may prevent an ingress of microorganisms from reaching portable device 100, but may allow the passage of air and sterilizing media to contact portable device 100. Sterilizing media may include, but is not limited to, ethylene oxide (ETO), steam, gamma irradiation, and electron beam (eBeam), and may help to maintain a sterile environment for portable device 100 prior to use. It should be appreciated that the sterile environment may provide sterile asepsis to eliminate micro-organisms from the portable device. It should further be appreciated that package 700, first tray 300 and second tray 500 may be made of material including, but not limited to, paper, laminated film, plastic, and foil that may provide a sterile barrier. It should be appreciated that third connecting cable (FIG. 3) and sixth connector 650 may detach from package 700.

It should be appreciated that package 700 may form a second packaging that may facilitate safe storage and handling of portable device 100. It should be appreciated that package 700 may contain any number of trays or primary packages without departing from the present disclosure.

It should further be appreciated that when first connecting cable 210 is detached from portable device 100, portion 110 of portable device 100 may be charged using power supply 800 (FIG. 4) that may be connected to charging port 120 (FIG. 2 and FIG. 6) using a plurality of connecting cables. Portion 110 may be fully charged while remaining in a sealed and sterile environment. Fully charging portion 110 may include charging at least one chargeable battery to a full capacity and/or up to 100% of its capacity. It should be appreciated that portion 110 may be charged without removing cover 320, without removing cover 520, and/or without opening package 700. It should be appreciated that a power supply may be delivered to portable device 100 using components including, but not limited to, connecting cables, a wireless charging pad, an induction charge, an electromagnetic field, radio waves, resonance stimulation, and low level microwave stimulation. It should be appreciated that at least one chargeable battery may be securely enclosed within portable device 100 in a sterile environment without compromising the aseptic nature of the contents of portable device 100 according to embodiments of the present disclosure. It should be appreciated that any number of batteries may be provided in series, in a battery pack, and/or assembled any form without departing from the disclosure. It should further be appreciated that at least one chargeable battery may be provided inside portion 110, external to portion of portable device 110, and/or external to portable device 100 without departing from the present disclosure. It should also be appreciated that batteries may include, but are not limited to, rechargeable batteries, storage batteries, a secondary cell, and/or an accumulator that can be charged, discharged, and recharged any number of times.

Figure 6:
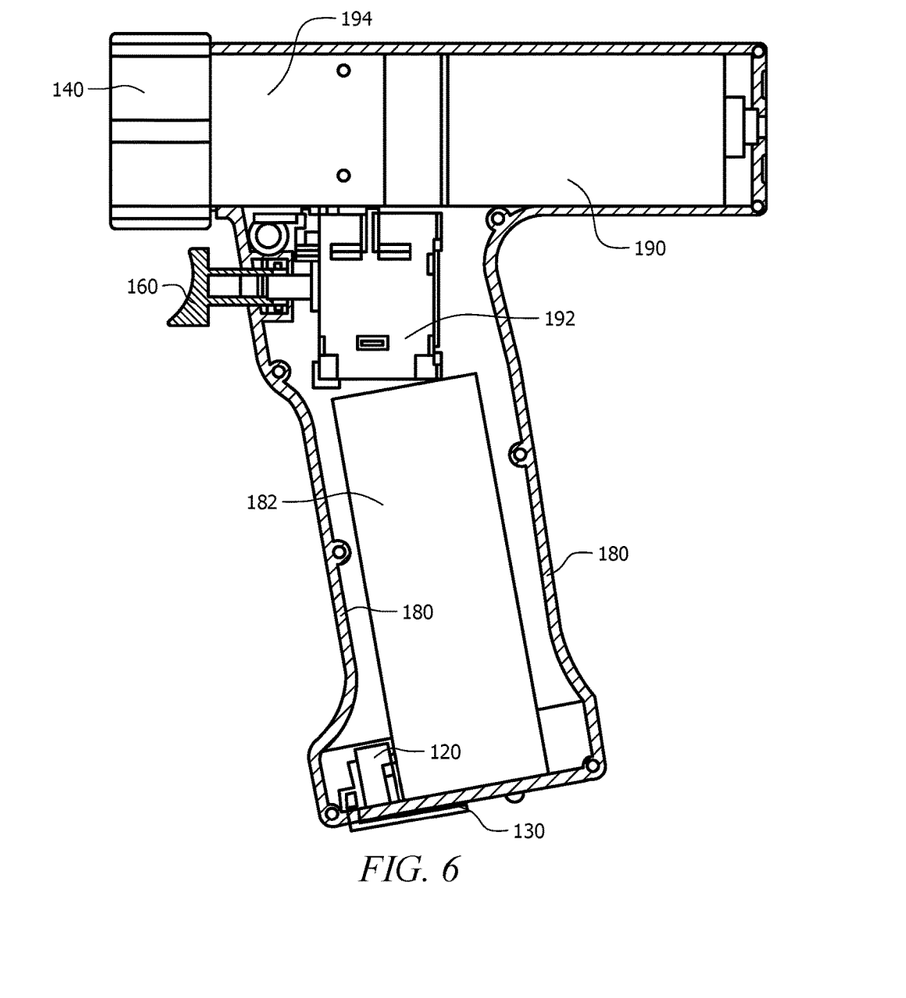
FIG. 6 depicts a sectional view of a portion of the portable device according to an embodiment of the present disclosure.

According to an embodiment of the present disclosure, as shown in FIG. 1, portion 110 of portable device 100 may provide attachment release ring 140, attachment coupling 150, and trigger 160. Attachment release ring 140 may rotate to a locked position and an unlocked position in embodiments of the present disclosure. Lock 170 may be provided to set attachment release ring 140 in the locked or in the unlocked position. It should be appreciated that lock 170 may be provided to lock the interior of attachment coupling 150 so that attachment coupling 150 may rotate in a clockwise direction or in a counterclockwise direction without departing from the present disclosure. It should be appreciated that a spring-loaded collar may be included in portable device 100 and may engage an attachment. It should further be appreciated that a spring-loaded collar may be pulled backwards along a central axis of portion 110, and when the spring-loaded collar is released, it may spring forward and securely hold the attachment in place. It should also be appreciated that an attachment may automatically engage with internal drive shaft 194 (FIG. 6). It should be appreciated that an attachment may be removed from attachment coupling 150 by pulling a spring-loaded collar backwards along a central axis of portion 110, and may provide for easily removing the attachment. Trigger 160 may be provided to vary the speed of rotation of the interior of attachment coupling. It should be appreciated that trigger 160 may be provided to control the direction of rotation of the interior of attachment coupling 150 in a clockwise direction or in a counterclockwise direction without departing from the present disclosure. It should be appreciated that portion 110 may provide a variable-speed trigger and an instant-reverse trigger in some embodiments of the present disclosure. Portion 110 may also provide at least one grip 180 that may stabilize portion 110 in the user's hands without departing from the present disclosure. It should be appreciated that the at least one grip 180 may be textured.

Figure 2:
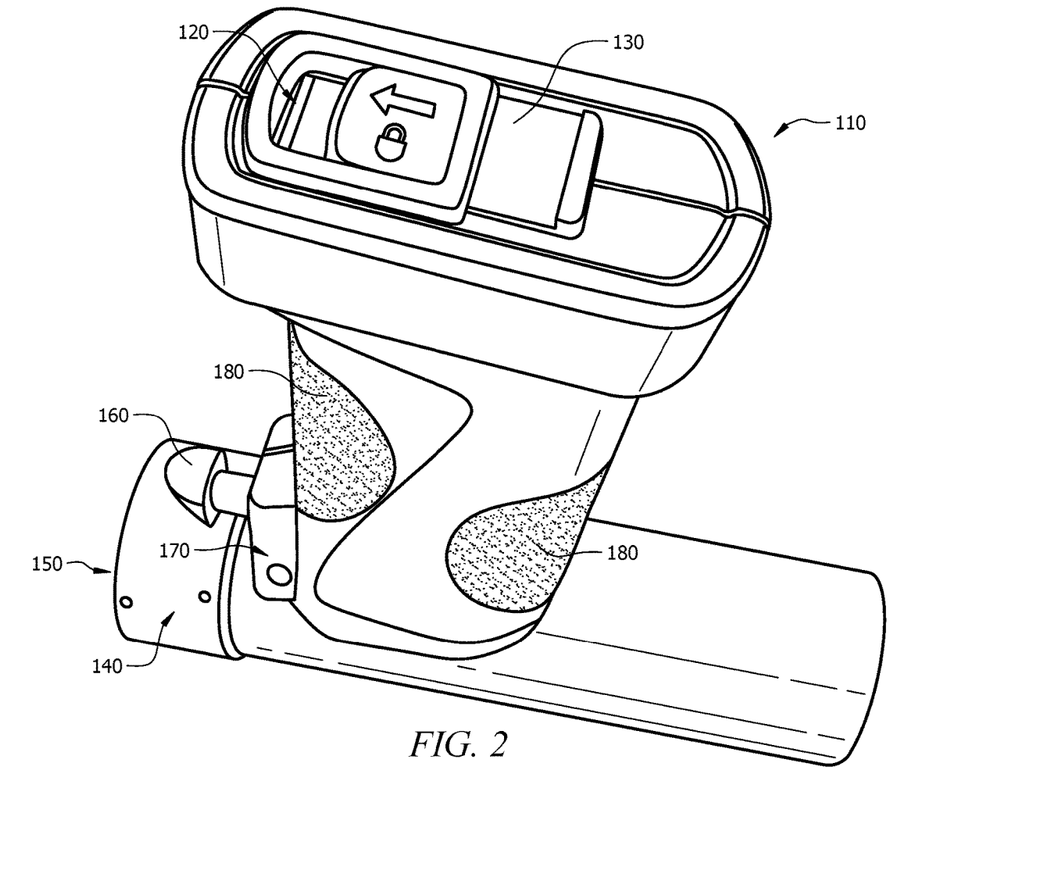
FIG. 2 depicts a perspective view of a portion of the portable device according to an embodiment of the present disclosure.

As shown in FIG. 2 according to an embodiment of the present disclosure, portion 110 may provide charging port 120 and charging port cover 130. Charging port 120 may include a female port that may be provided to receive first connector 230 (FIG. 1 and FIG. 5), and charging port 120 may be covered and protected by charging port cover 130. It should be appreciated that a female port may include, but is not limited to, a female USB port, a female cord end, and/or female wire end without departing from the present disclosure. It should be appreciated that charging port cover 130 may slide between a locked position and unlocked position 130 in embodiments of the present disclosure. It should be appreciated that the locked position may prevent first connecting cable 210 (FIG. 1 and FIG. 5) or another cable from attaching to charging port 120.

According to an embodiment of the present disclosure, as shown in FIG. 3, fourth connector 450 may receive fifth connector 630. Fifth connector 630 may include a male connector and may be provided at fifth end 620 of connecting cable 610. Sixth connector 650 may be provided at sixth end 640 of connecting cable 610 and may include a female port that may be accessible from an exterior of package 700 using sixth connector 650. Wall 710 of package 700 may house sixth connector 650. It should be appreciated that package 700 may include at least one pre-installed connecting cable without departing from the present disclosure.

Figure 4:
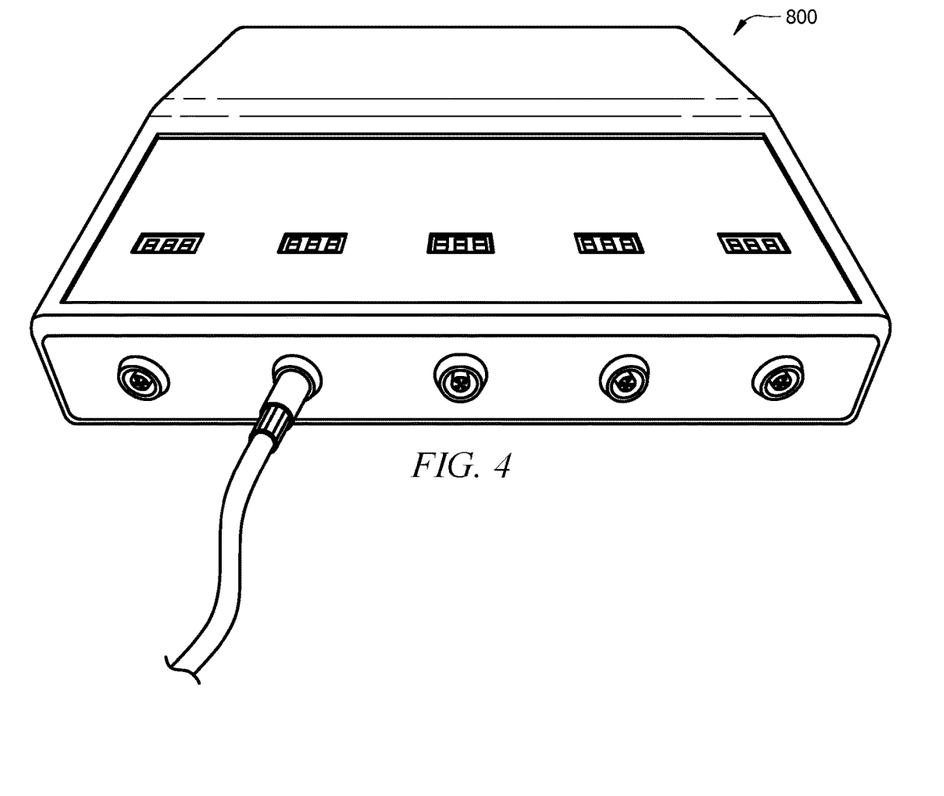
FIG. 4 depicts a power supply according to an embodiment of the present disclosure.

According to an embodiment of the present disclosure, as shown in FIG. 4, power supply 800 may be connected to the portable device and may read the charge level of the batteries. Power supply 800 may shut down when a full charge is reached, and may indicate to the user when portion 110 has attained a full charge, such as through an LED window. It should be appreciated that power supply 800 may be a battery charger in some embodiments of the present disclosure. It should be appreciated that any type of display window may be incorporated into power supply 800 without departing from the present disclosure. It should be appreciated that the charge level may indicate whether portion 110 is charged to a full capacity. It should be appreciated that a power supply may be provided within the sterile environment or external to the sterile environment according to embodiments of the present disclosure.

Figure 5:
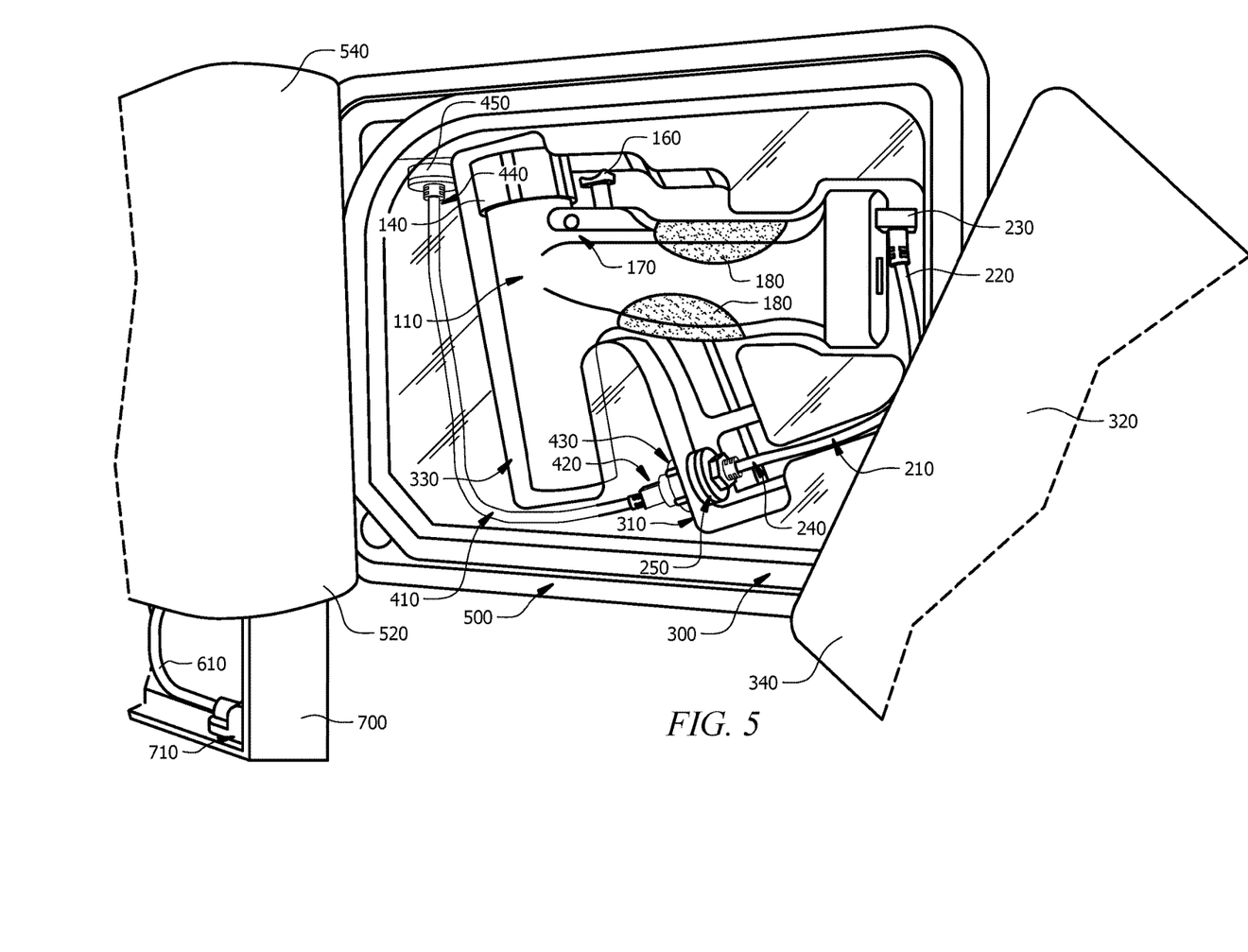
FIG. 5 depicts a portable device including open microbial barriers according to an embodiment of the present disclosure.

As shown in FIG. 5 according to an embodiment of the present disclosure, a portable device may provide cover 320 and cover 520 that may be opened and/or removed from first tray 300 and second tray 500, respectively. After removing cover 320 and cover 520, a user may remove portion 110 from compartment 330 and use portion 110 as desired. It should be appreciated that portion 110 may be removed from compartment 330 with up to 100% supply of power. It should further be appreciated that portion 110 may be charged when removed from compartment 330 without departing from the present disclosure.

As shown in FIG. 6 according to an embodiment of the present disclosure, portion 110 may provide battery 182. Battery 182 may be arranged inside of portion 110 and may be charged by connecting a cable to charging port 120. Portion 110 may include motor 190 and control panel 192. Motor 190 may control the speed of attachments that may be provided inside of attachment coupling 150. Control panel 192 may provide the electrical components required to operate at least trigger 160, motor 190, and attachment coupling 150. Internal drive shaft 194 may be connected to attachment coupling 150 and provide for an engagement of portable device 100 with an attachment. It should be appreciated that an engagement with an attachment may be accomplished using a spring-loaded collar without departing from the present disclosure.

It should be appreciated that each end of each connecting cable may be secured within a respective wall or package using mechanically compressed seals, glue, and/or a similar sealing agent that may be provided to maintain microbe-free connections. It should be appreciated that attachment coupling 150 may be provided to receive an attachment. It should be appreciated that an attachment may be selected from a plurality of attachment types and inserted into attachment coupling 150. The plurality of attachment types may include, but are not limited to, saw blades, wire/pin drivers, and drill chucks. It should further be appreciated that an attachment may be inserted into attachment coupling 150 when lock is in use. The end of the attachment provided inside of attachment coupling 150 may engage an interior of attachment coupling 150 and maintain a secured position. It should be appreciated that a free end of the attachment that is opposite of the end of attachment disposed within attachment coupling 150 may be pulled slightly to ensure that the attachment is secured inside of attachment coupling 150.

It should be appreciated that when attachment release ring 140 is rotated to unlocked position, an attachment may be removed by pulling the attachment away from attachment coupling 150. It should be appreciated that when the portable device is locked, injury to patients may be prevented. When coupling attachments, removing attachments, and/or before laying the portable device down, the portable device may be locked and may prevent injury to a user and/or patient.

It should be appreciated that portion 110 and any attachments thereto may cool down following a maximum time of constant use. The maximum time of constant use and a minimum time of non-use may be predetermined time periods. For example, the maximum time of constant use for drilling may be 60 seconds, and the minimum time of non-use may be 60 seconds over nine cycles. Regarding sawing, for example, the maximum time of constant use for drilling may be 30 seconds, and the minimum time of non-use may be 60 seconds over nine cycles. It should be appreciated that additional portable devices may be used if extended periods of constant use are required. It should be appreciated that the temperature of portable device 100 may be controlled and may prevent overheating of the device and harm to patients.

It should be appreciated that portable device 100 may be a battery-driven tool system that may be used for medical procedures including, but not limited to, drilling, reaming, pin and wire placement, and cutting bone and hard tissue. It should be appreciated that portable device 100 may be operated for non-medical use including, but not limited to, construction, household-use, and food preparation. It should be appreciated that portable device 100 may provide power for immediate use after opening cover 320, cover 520, and/or package 700. It should be appreciated that portable device 100 may provide cost advantages over reusable portable devices. It should further be appreciated that a portable device according to embodiments of the present disclosure may be used one time and may be recycled and/or discarded after use. It should be appreciated that portable device 100 may eliminate a need for maintenance and lubrication. It should also be appreciated that a portable device according to embodiments of the present disclosure may eliminate a need for back-up batteries and/or a back-up power supply. It should further be appreciated that portable device 100 may not require special processes for cleaning and/or disposal of any component.

It should be appreciated that embodiments of the present disclosure may provide for usage in conflict zones or natural disasters, where charging equipment may not be possible. Further, usage may be provided in geographic locations that may not have access to an adequate power supply and/or sterile environment cannot fully charge medical equipment and instruments. However, usage in hospitals and other medical facilities may be improved insofar as devices containing tools necessary for medical procedures may be readily available off-the-shelf and for immediate use at a cost that has significant advantages over other reusable tool systems.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. A method for supplying power to a portable device powered by at least one chargeable battery, the method comprising:
    sealing the portable device in a sterile environment using a first tray, a first microbial barrier, a second tray, and a second microbial barrier, wherein the first tray is configured to receive and secure the portable device, wherein the first microbial barrier is arranged to seal the first tray and maintain a sterile environment for the portable device, wherein the second tray is configured to receive and secure the first tray in the second tray, and wherein the second microbial barrier is arranged to seal the second tray and maintain a sterile environment for the portable device; and
    charging the portable device in the sterile environment, wherein a power supply supplies power to the at least one chargeable battery contained in the portable device, wherein a first connecting cable and a second connecting cable connect the at least one chargeable battery to a charging port, wherein the first connecting cable is secured within the first tray and the second connecting cable is secured within the first tray and the second tray.

2. The method for supplying power to the portable device powered by the at least one chargeable battery of claim 1, further comprising:

arranging the at least one chargeable battery inside of a portion of the portable device.

3. The method for supplying power to the portable device powered by the at least one chargeable battery of claim 1, further comprising:
arranging the at least one chargeable battery external to a portion of the portable device.

4. The method for supplying power to the portable device powered by the at least one chargeable battery of claim 1, further comprising:
arranging the at least one chargeable battery external to the portable device.

5. The method for supplying power to the portable device powered by the at least one chargeable battery of claim 1, further comprising:
charging the portable device to a full capacity prior to opening the sterile environment.

6. A portable device powered by at least one chargeable battery, comprising:
a portion of the portable device including a charging port;
a first tray configured to receive and secure the portion of the portable device;
a first microbial barrier arranged to seal the first tray and maintain a sterile environment for the portable device;
a second tray configured to receive and secure the first tray in the second tray;
a second microbial barrier arranged to seal the second tray and maintain a sterile environment for the portable device;
a package configured to receive the second tray; and
the at least one chargeable battery configured to power the portion of the portable device, wherein a first connecting cable and a second connecting cable connect the at least one chargeable battery to the charging port, wherein the first connecting cable is secured within the first tray and the second connecting cable is secured within the first tray and the second tray, and wherein a power supply is arranged to supply power to the at least one chargeable battery.

7. The portable device powered by the at least one chargeable battery of claim 6, wherein the at least one battery is arranged inside of the portion of the portable device.

8. The portable device powered by the at least one chargeable battery of claim 6, wherein the at least one battery is arranged external to the portion of the portable device.

9. The portable device powered by the at least one chargeable battery of claim 6, wherein the at least one battery is arranged external to the portable device.

10. The portable device powered by the at least one chargeable battery of claim 6, further comprising:
a plurality of microbial barriers provided to seal the sterile environment.

11. The portable device powered by the at least one chargeable battery of claim 6, wherein the portable device is charged to a full capacity prior to opening the sterile environment.

12. A system for supplying power to a portable device provided in a sterile environment, comprising:
securing a portion of the portable device in a first tray, wherein the portion of the portable device includes a charging port for receiving power;
covering the first tray with a first microbial barrier;
connecting the portion of the portable device to the first tray using a first connecting cable, wherein the first connecting cable is secured in the first tray;
securing the first tray in a second tray;
covering the second tray with a second microbial barrier;
connecting the first tray and the second tray using a second connecting cable, wherein the second connecting cable is secured in the first tray and the second tray;
connecting the second tray to a package using a third connecting cable;
securing the second tray in the package; and
supplying power to the portable device using at least one chargeable battery.

13. The system for supplying power to the portable device provided in the sterile environment of claim 12, wherein the at least one chargeable battery is arranged inside the portion of the portable device.

14. The system for supplying power to the portable device provided in the sterile environment of claim 12, wherein the at least one chargeable battery is arranged external to the portion of the portable device.

15. The system for supplying power to the portable device provided in the sterile environment of claim 12, wherein the at least one chargeable battery is arranged external to the portable device.

16. The system for supplying power to the portable device provided in the sterile environment of claim 12, wherein the portable device is charged to a full capacity prior to opening the sterile environment.

* * * * *